(12) United States Patent
Matsushita (10) Patent No.: US 10,290,484 B2
(45) Date of Patent: May 14, 2019

(54) MASS SPECTROMETER

(71) Applicant: SHIMADZU CORPORATION, Kyoto-shi, Kyoto (JP)

(72) Inventor: Tomoyoshi Matsushita, Manchester (GB)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/777,409

(22) PCT Filed: Nov. 20, 2015

(86) PCT No.: PCT/JP2015/082745
§ 371 (c)(1),
(2) Date: May 18, 2018

(87) PCT Pub. No.: WO2017/085876
PCT Pub. Date: May 26, 2017

(65) Prior Publication Data
US 2019/0006162 A1 Jan. 3, 2019

(51) Int. Cl.
*H01J 49/00* (2006.01)
*H01J 49/04* (2006.01)
(Continued)

(52) U.S. Cl.
CPC .......... *H01J 49/0409* (2013.01); *G01N 27/62* (2013.01); *G01N 27/64* (2013.01)

(58) Field of Classification Search
CPC ...... H01J 49/0409; G01N 27/62; G01N 27/64
(Continued)

(56) References Cited

U.S. PATENT DOCUMENTS

2005/0045815 A1\* 3/2005 Bui ............... H01J 49/0004
250/282
2009/0057552 A1\* 3/2009 Yamada ............ H01J 49/0418
250/288

FOREIGN PATENT DOCUMENTS

DE 10 2008 035 079 A1 3/2009
JP 2009-052994 A 3/2009
(Continued)

OTHER PUBLICATIONS

International Search Report for PCT/JP2015/082745 dated Jan. 19, 2016 [PCT/ISA/210].

*Primary Examiner* — Michael Maskell
(74) *Attorney, Agent, or Firm* — Sughrue Mion, PLLC (57) ABSTRACT

A mass spectrometer 10 includes: an insertion port 1 through which a sample plate 8 is to be inserted; a reading device 6 including: a light emitter 61 disposed to emit light in such a manner that the light falls onto the sample plate 8 inserted through the insertion port 1; and a light receiver 62 for receiving reflected by or transmitted through the sample plate 8 to read an identifier 80 provided on the sample plate 8; an analyzer 101 for performing a mass spectrometric analysis on a sample 9 placed on the sample plate 8, to obtain analysis information of the sample 9; and a storage section 51 for storing identification information 800 of the sample plate 8 and the analysis information 100 of the sample 9 placed on the sample plate 8, which are associated with each other, the identification information 800 being indicated by the identifier 80 read by the reading device 6, and the analysis information 100 being obtained by the analyzer 101.

2 Claims, 5 Drawing Sheets (51) Int. Cl.
*G01N 27/62* (2006.01)
*G01N 27/64* (2006.01)

(58) Field of Classification Search
USPC .......................................... 250/281, 282, 288
See application file for complete search history.

(56) References Cited

FOREIGN PATENT DOCUMENTS

| | | |
|---|---|---|
| JP | 2012-230801 A | 11/2012 |
| JP | 2013-190315 A | 9/2013 |

\* cited by examiner

MASS SPECTROMETER

CROSS REFERENCE TO RELATED APPLICATIONS

This application is a National Stage of International Application No. PCT/JP2015/082745 filed Nov. 20, 2015.

TECHNICAL FIELD

The present invention relates to a mass spectrometer that performs a mass spectrometric analysis on a sample placed on a sample plate.

BACKGROUND ART

In recent years, the application of mass spectrometric technique has been advancing in the field of clinical examination. For example, a mass spectrometer which can be suitably used in hospitals to perform a specimen examination for identifying components contained in a specimen obtained from a patient or microorganisms contained in the specimen has been developed (see Patent Literature 1, for example).

For analysis of a sample, such as a specimen, by a mass spectrometer, the task of placing a sample on a sample plate ("sample preparation operation") is conducted in advance. Along with the sample preparation operation, the task of associating a sample plate and a sample to be placed on the sample plate is performed. For example, this task is carried out in such a manner that an operator using a barcode reader consecutively reads a barcode provided on the sample plate (the barcode corresponding to an identifier of the sample plate) and a barcode provided on a container and the like containing a sample to be placed on the sample plate (the barcode corresponding to an identifier of the sample), and sends the read information to a computer (a data server) connected to the mass spectrometer. The data server associates the barcode of the sample plate (specifically, identification information of the sample plate indicated by the barcode) with the barcode of the sample (specifically, identification information of the sample indicated by the barcode), and stores the associated information. Accordingly, the sample plate and the sample placed on the sample plate are associated with each other.

An operator of the mass spectrometer sets the sample plate on which the sample is placed, in the mass spectrometer one by one, to operate the mass spectrometer to analyze the sample. Before setting the sample plate in the mass spectrometer, the operator reads the barcode provided on the sample plate with a barcode reader, and inputs the read information into the mass spectrometer. Based on this information, the mass spectrometer recognizes which one of the sample plates corresponds to the analysis information obtained by the mass spectrometric analysis. As mentioned above, the sample plate and the sample placed thereon have previously been associated with each other in the data server connected to the mass spectrometer. Accordingly, the association of the sample plate with the analysis information can be recognized, thereby allowing the analysis information and the sample to be associated with each other.

CITATION LIST

Patent Literature

Patent Literature 1: JP 2012-230801 A

SUMMARY OF INVENTION

Technical Problem

In the specimen examination or similar tasks, analysis information must be correctly associated with a sample without fail, since the misidentification of samples causes serious accidents. However, in the conventional case, since an operator of a mass spectrometer manually reads identifiers provided on the sample plates, it is impossible to completely prevent the omission of reading, failure of reading, or other human errors. Accordingly, it is impossible to completely avoid the situation in which the operator cannot recognize which sample corresponds to the analysis information obtained by the mass spectrometer.

An object of the present invention is to provide a technique capable of increasing reliability in association between a sample and the corresponding analysis information in a mass spectrometer.

Solution to Problem

A mass spectrometer according to the present invention, which is developed to solve the above problems, includes:

an insertion port through which a sample plate is to be inserted;

a reading device including: a light emitter disposed to emit light in such a manner the light falls onto the sample plate inserted through the insertion port; and a light receiver for receiving light reflected by or transmitted through the sample plate to read an identifier provided on the sample plate;

an analyzer for performing a mass spectrometric analysis on a sample placed on the sample plate, to obtain analysis information of the sample; and a storage section for storing identification information of the sample plate and the analysis information of the sample placed on the sample plate while the identification information and the analysis information are associated with each other, the identification information being indicated by the identifier read by the reading device, and the analysis information being obtained by the analyzer.

In the mass spectrometer, when the sample plate is inserted through the insertion port, the identifier provided on the sample plate is read by the reading device. Then, the identification information of the sample plate, which is indicated by the read identifier, and the analysis information of the sample placed on the sample plate, are associated with each other and stored. This configuration eliminates the necessity to manually read the identifier provided on the sample plate, thereby preventing the omission of reading, failure of reading, or other human errors. Therefore, the reliability in association between a sample and the corresponding analysis information can be enhanced.

In a preferable mode of the mass spectrometer, the light receiver receives light reflected from the sample plate, and an identifier indicating the absence of the sample plate is disposed at a position opposite from the reading device across the sample plate inserted through the insertion port.

In this mass spectrometer, when the sample plate is not present between the reading device and the identifier indicating the absence of the sample plate (i.e., when there is no sample plate inserted through the insertion port), the reading device reads the identifier indicating the absence of the sample plate. Thus, the reading device for reading the identification information of the sample plate can be used to detect the presence/absence of the sample plate, without specifically providing a detector or the like for detecting the presence/absence of the sample plate.

In a preferable mode of the mass spectrometer,
the identifier is a barcode, and
the reading device is a barcode reader.

The barcode reader is small in size and low in cost, thereby contributing to the reduction in size of the mass spectrometer and reduction in manufacturing cost.

Advantageous Effects of the Invention

When a sample plate is inserted through the insertion port, the identifier provided on the sample plate is read by the reading device. This configuration eliminates the necessity to manually read identifiers provided on the sample plate, thereby preventing the omission of reading, failure of reading, or other human errors. Therefore, the reliability in association between a sample and the corresponding analysis information can be enhanced.

DESCRIPTION OF EMBODIMENTS

Hereinafter, preferable embodiments according to the present invention are described, with reference to the drawings.

1. Sample Plate 8

Figure 1:
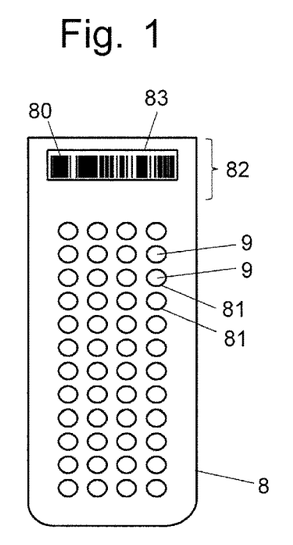
FIG. 1 is a plan view of a sample plate.

In a mass spectrometer according to an embodiment of the present invention, a target object (a sample) placed on a sample plate is irradiated with a laser beam to be ionized, and the obtained ions are detected after being separated according to their mass-to-charge ratios during their flight. The sample plate on which a sample is placed is described with reference to FIG. 1, before the mass spectrometer is described. FIG. 1 is a plan view showing a sample plate 8.

The sample plate 8 is a plate member having a top surface where a plurality of concave portions 81 are formed in a matrix form for example. Samples 9 are placed on this sample plate 8 by dropping a sample 9 onto each of the plurality of concave portions 81.

The sample plate 8 has, at one end thereof, an area 82 where no concave portion 81 is formed. An operator can hold the sample plate 8 without touching the sample 9, by taking hold of the area 82. The area 82 may hereinafter be referred to as a "handling area 82".

The handling area 82 is provided with an identifier 80 that indicates identification information 800 of the sample plate 8 (see FIG. 6; this information may hereinafter be referred to as the "plate information"). In the present embodiment, the identifier 80 is in the form of a barcode. A seal 83 on which the barcode is printed is adhered to the handling area 82 to provide the sample plate 8 with the identifier 80. The identifier 80 provided on the sample plate 8 may hereinafter be referred to as the "plate identifier 80".

2. Mass Spectrometer 10 According to the Embodiment

Figure 2:
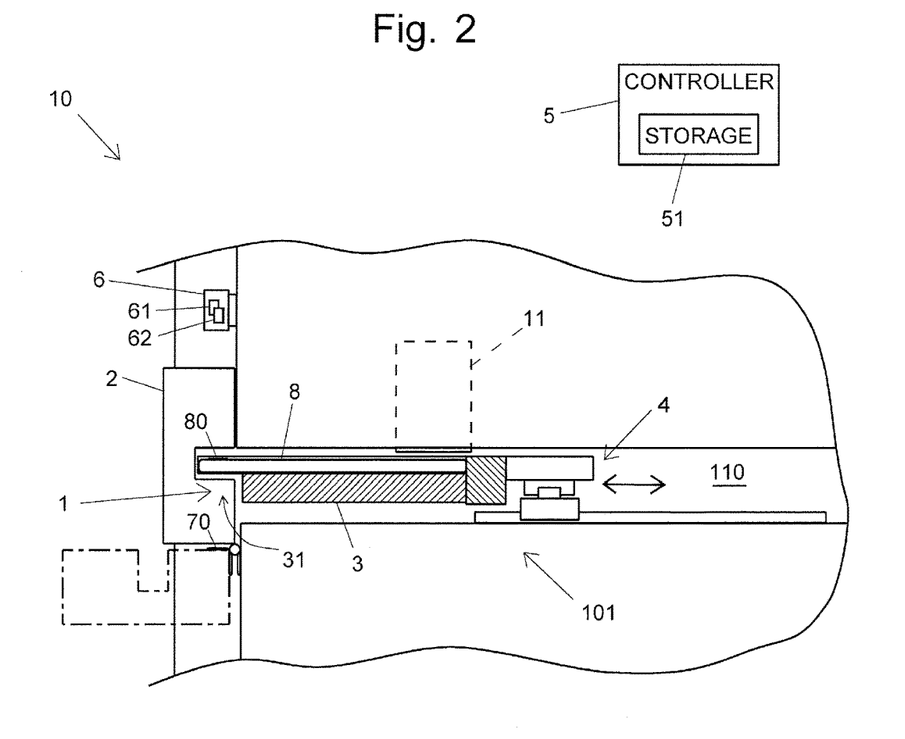
FIG. 2 is a side view showing a section of a mass spectrometer.

The mass spectrometer according to the embodiment is described, with reference to FIG. 2. FIG. 2 is a side view showing a section of the mass spectrometer 10. It should be noted that, one of the side walls of the mass spectrometer 10 is omitted from FIG. 2, and stage 3 is shown in a cross-sectional form.

The mass spectrometer 10 includes an insertion port 1 for inserting the sample plate 8 into an inner space 110 of the device, and a door 2 that opens and closes the insertion port 1. In the inner space 110, the stage 3 on which the sample plate 8 is to be placed, and a moving mechanism 4 for moving the stage 3 within the inner space 110, are disposed. In addition, the mass spectrometer 10 includes a controller 5 that controls relevant elements included in the mass spectrometer 10 to perform a series of processes on the sample 9 on the sample plate 8.

In the inner space 110, a mass spectrometric analysis is carried out on the sample 9 on the sample plate 8. Specifically, the sample 9 on the sample plate 8 that is placed on the stage 3 is irradiated with a laser beam from a laser beam source (not shown) so as to be ionized, and then ionized substances are extracted by an extraction electrode 11. As mentioned above, the sample 9 is held in each of the plurality of concave portions 81 on the sample plate 8. The above processing is carried out while the moving mechanism 4 moves the stage 3 relative to the laser beam source, in order to sequentially deliver the laser beam to each of the samples 9 held in the concave portions 81. The substances extracted by the extraction electrode 11 are accelerated and separated according to their mass-to-charge ratios, so as to be detected (configurations relating to the separation and the detection are not shown). In the inner space 110, an evaluation system that is not shown is provided, which maintains the inner space 110 in a vacuum state during the processing on the sample plate 8.

As mentioned above, in the mass spectrometer 10, the stage 3, the moving mechanism 4, the extraction electrode 11, the controller 5, and other various units that are not shown cooperate with each other, to carry out a mass spectrometric analysis on the samples 9 placed on the sample plate 8, thereby obtaining analysis information 100 (see FIG. 6) of each sample 9. In other words, the stage 3, the moving mechanism 4, the extraction electrode 11, the controller 5, and other various units (that are not shown) constitute an analyzer 101 which carries out a mass spectrometric analysis on the samples 9 placed on the sample plate 8 to obtain the analysis information 100 of each sample 9.

It should be noted that the inner space 110 may be divided into a plurality of spaces. For example, it may be divided into a processing space for carrying out the processing, and a load lock space for the transfer of the sample plate 8 between the space outside the mass spectrometer 10 and the processing space. In such a case, the load lock space is disposed between the insertion port 1 and the processing space. The processing space and the load lock space are separated by a gate valve or the like, and each of those spaces is configured to be independently switchable between a vacuum state and the atmospheric state.

3. Transfer of Sample Plate 8

Figure 3:
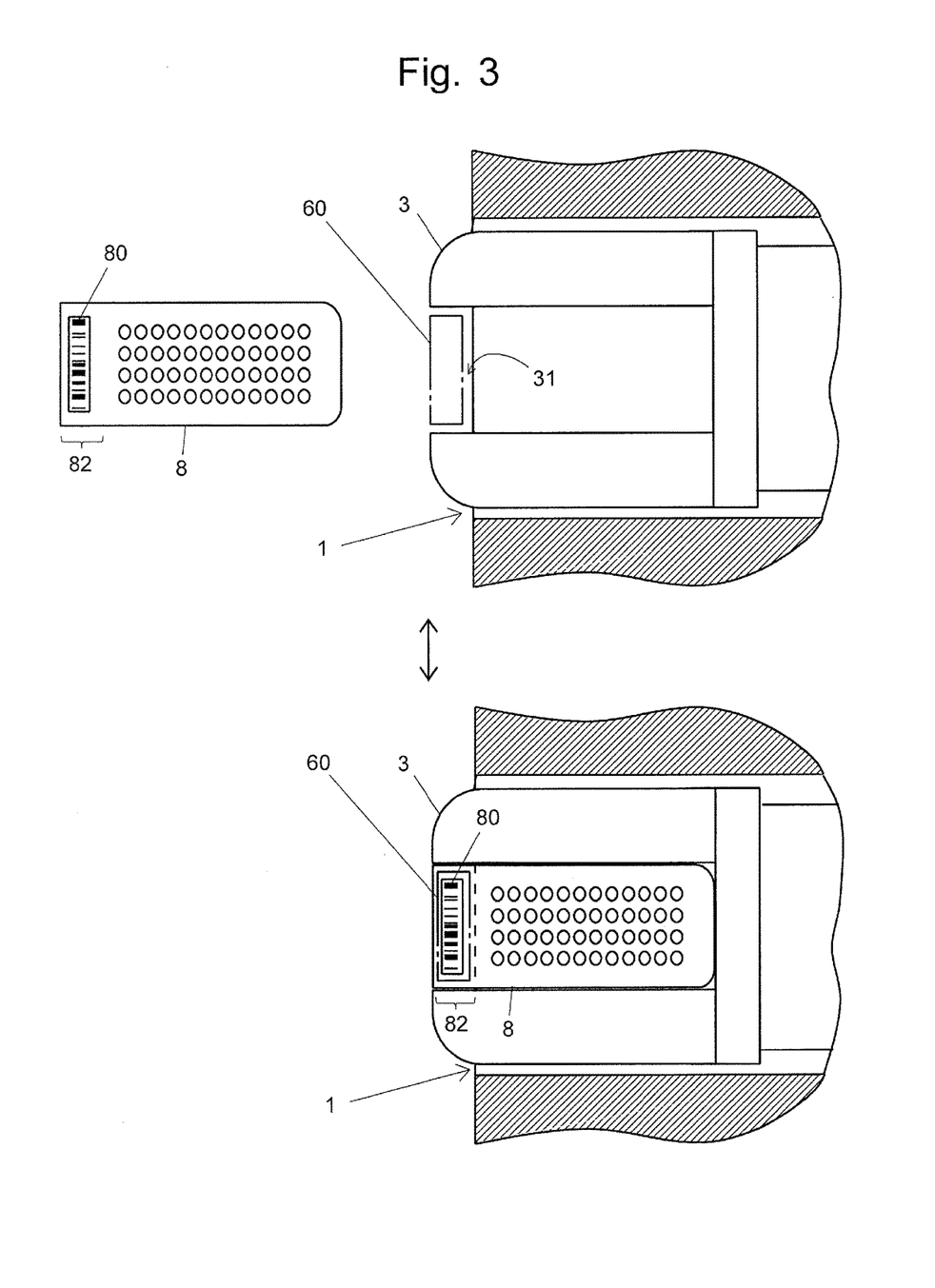
FIG. 3 shows the transfer of the sample plate onto or from a stage disposed at an initial position.

An embodiment of inserting the sample plate 8 into the mass spectrometer 10 is described, with reference to FIG. 3 in addition to FIG. 2. FIG. 3 shows the transfer of the sample plate 8 onto or from the stage 3 disposed at an initial position.

When the sample plate 8 that has undergone a mass spectrometric analysis in the mass spectrometer 10 is extracted from the insertion port 1 by an operator, the mass spectrometer 10 becomes ready to accept another sample plate 8. In this condition, the door 2 is opened (as indicated by the long dashed short dashed line in FIG. 2), and the stage 3 is disposed at the initial position as shown in FIGS. 2 and 3. When the stage 3 is disposed at the initial position, a part of the stage 3 protrudes from the insertion port 1. Specifically, the stage 3 has a cut out area that is an area 31 (which may be hereinafter referred to as a "notch area 31") to be positioned under the handling area 82 when the sample plate 8 is placed on the stage 3. When the stage 3 is at the initial position, the notch area 31 is disposed outside the insertion port 1. Accordingly, an operator can place the sample plate 8 on the stage 3 by inserting the sample plate 8 through the insertion port 1 while holding the sample plate 8 by pinching the upper and lower sides of the handling area 82. The operator can also extract the sample plate 8 from the insertion port 1, by holding the sample plate 8 on the stage 3 by pinching the upper and lower sides of the handling area 82.

When the sample plate 8 is placed on the stage 3 at the initial position (as shown in the lower side of FIG. 3), the door 2 is closed and the pressure in the inner space 110 is reduced. When the inner space 110 reaches a predetermined degree of vacuum, the moving mechanism 4 starts moving the stage 3, and the mass spectrometric analysis on the sample 9 on the sample plate 8 placed on the stage 3 is initiated. When the mass spectrometric analysis is completed, the stage 3 is returned to the initial position. After the inner space 110 is restored to the atmospheric state, the door 2 is opened (as shown in the lower side of FIG. 3). When the sample plate 8 is extracted by an operator, the mass spectrometer 10 becomes ready to accept another sample plate 8 (as shown in the upper side of FIG. 3).

4. Reading Device 6

Figure 4:
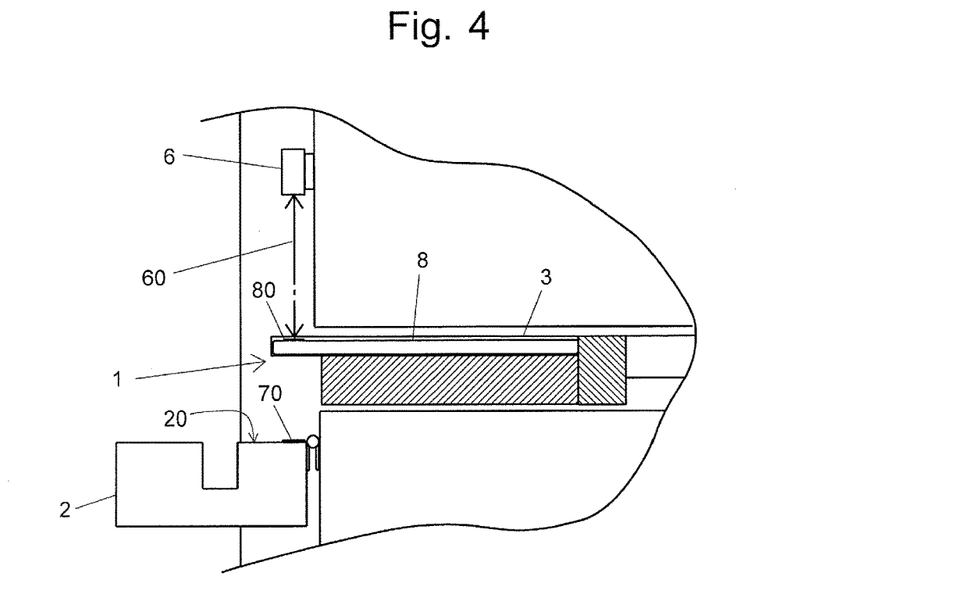
FIG. 4 shows a reading device reading an identifier provided on the sample plate.
Figure 5:
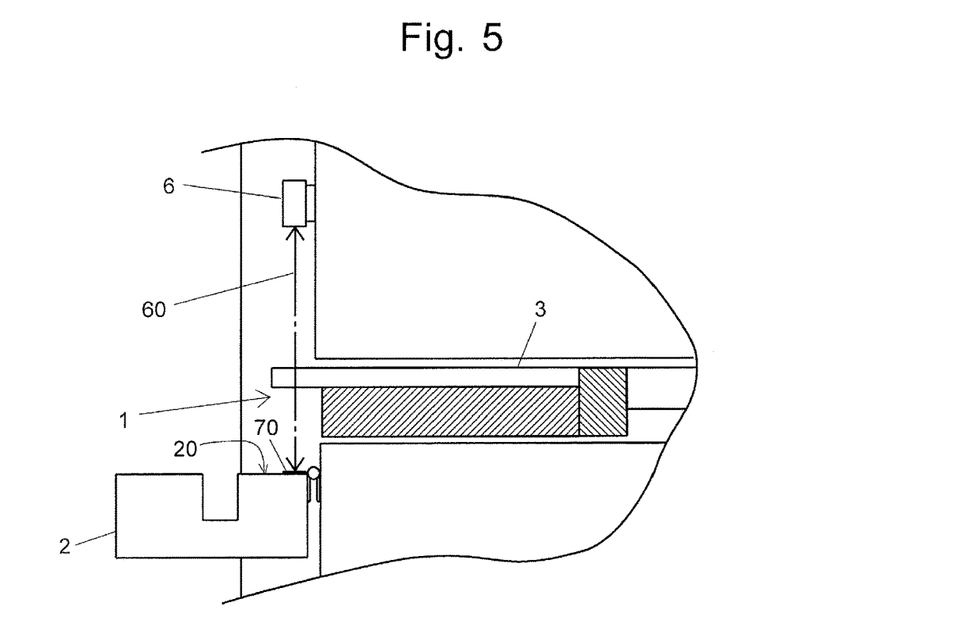
FIG. 5 shows the reading device reading a blank identifier.

The mass spectrometer 10 includes a reading device 6 that reads the identifier (plate identifier) 80 provided on the sample plate 8. The reading device 6 is described, with reference to FIGS. 4 and 5 in addition to FIGS. 2 and 3. FIG. 4 shows the reading device 6 reading the plate identifier 80. FIG. 5 shows the reading device 6 reading a blank identifier 70.

The reading device 6 casts light onto a target object and receives light reflected from the target object, to optically read the target object. Specifically, the reading device 6 includes a light emitter 61 that emits light for reading 60, and a light receiver 62 that receives reflected light of the light for reading 60 emitted from the light emitter 61. A target to be read by the reading device 6 should be the plate identifier 80 provided on the sample plate 8. The plate identifier 80 is in the form of a barcode in the present embodiment. Accordingly, the reading device 6 includes a barcode reader that can read a barcode.

The reading device 6 (specifically, the light emitter 61 of the reading device 6) is disposed so that the thereby generated light for reading 60 falls onto the sample plate 8 inserted through the insertion port 1 (i.e., the sample plate 8 placed on the stage 3 at the initial position). More specifically, the light emitter 61 is disposed above the insertion port 1 so that the light for reading 60 falls onto the handling area 82 of the sample plate 8 placed on the stage 3 at the initial position (i.e., so that the light for reading 60 falls onto the notch area 31 of the stage 3 at the initial position).

Accordingly, when the door 2 is opened and the sample plate 8 inserted through the insertion port 1 is present (in other words, the sample plate 8 is placed on the stage 3 at the initial position), the light for reading 60 emitted from the light emitter 61 falls onto the handling area 82 of the sample plate 8, and the light receiver 62 receives the reflected light from the plate identifier 80 adhered to the handling area 82 (as shown in FIG. 4).

The identifier 70 that indicates the absence of the sample plate 8 (this identifier may hereinafter be referred to as a "blank identifier") is disposed on a position opposite from the reading device 6 across the sample plate 8 inserted through the insertion port 1 (i.e., the sample plate 8 placed on the stage 3 at the initial position). More specifically, the blank identifier 70 is disposed at a position opposite from the reading device 6 across the handling area 82 of the sample plate 8 placed on the stage 3 at the initiation position (i.e., the notch area 31 of the stage 3 at the initial position). In the mass spectrometer 10, the inner surface 20 of the door 2 (in the opened state) is disposed at a position opposite from the reading device 6 across the notch area 31 of the stage 3 at the initial position. Accordingly, the blank identifier 70 is provided on this inner surface 20 in the present embodiment. The blank identifier 70 is in the form of a barcode, like the plate identifier 80. A seal on which the barcode is printed is adhered to the inner surface 20 of the door 2, thereby providing the blank identifier 70 on the inner surface 20.

Accordingly, when the door 2 is opened and there is no sample plate 8 inserted through the insertion port 1 (in other words, when the sample plate 8 is not placed on the stage 3 at the initial position), the light for reading 60 emitted from the light emitter 61 passes through the notch area 31 of the stage 3 and falls onto the blank identifier 70. Then, the light receiver 62 receives the reflected light from the blank identifier 70 (as shown in FIG. 5).

5. Table 50

Figure 8:
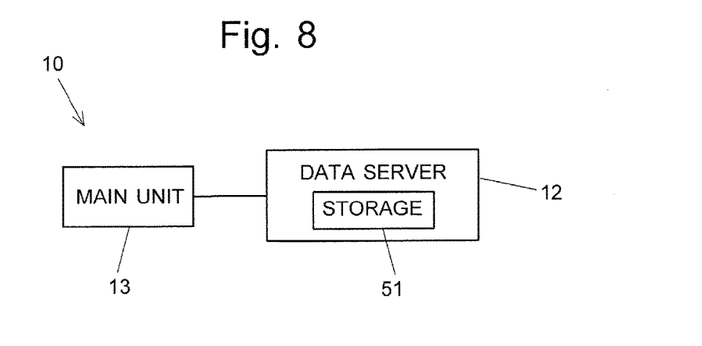
FIG. 8 is a block diagram showing the mass spectrometer including a main unit and a data server connected to the main unit.

The controller 5 includes a storage section 51 (see FIG. 2). The storage section 51 stores a table 50. The mass spectrometer 10 may include a main unit 13 and a computer (data server) 12 connected to the main unit 13, as shown in FIG. 8. In this case, at least part of the function of the controller 5 may be implemented by the data server 12, and the table 50 may be stored in the storage section 51 in the data server 12. FIG. 6 shows a configuration example of a management screen of the table 50, which is displayed on a display of the data server 12, for example.

The table 50 describes: plate information 800 indicated by the plate identifier 80; identification information 900 of the sample 9 (hereinafter also referred to as "sample information"); and analysis information 100 (more specifically, identification information for identifying analysis information, for example) obtained by performing a mass spectrometric analysis on the sample 9 using the analyzer 101. As mentioned above, there are a plurality of concave portions 81 formed on the sample plate 8. The table 50 contains position information 801 for identifying each of those concave portions 81. In the table 50, combination of the plate information 800 and the position information 801 (i.e., information for identifying each individual concave portion 81) is written in a single record. In the single record, a single piece of sample information 900 and a single piece of analysis information 100 are written. Thus, each of the information 800, 801, 900, and 100 written in the single record are associated with each other on the table 50.

Figure 6:
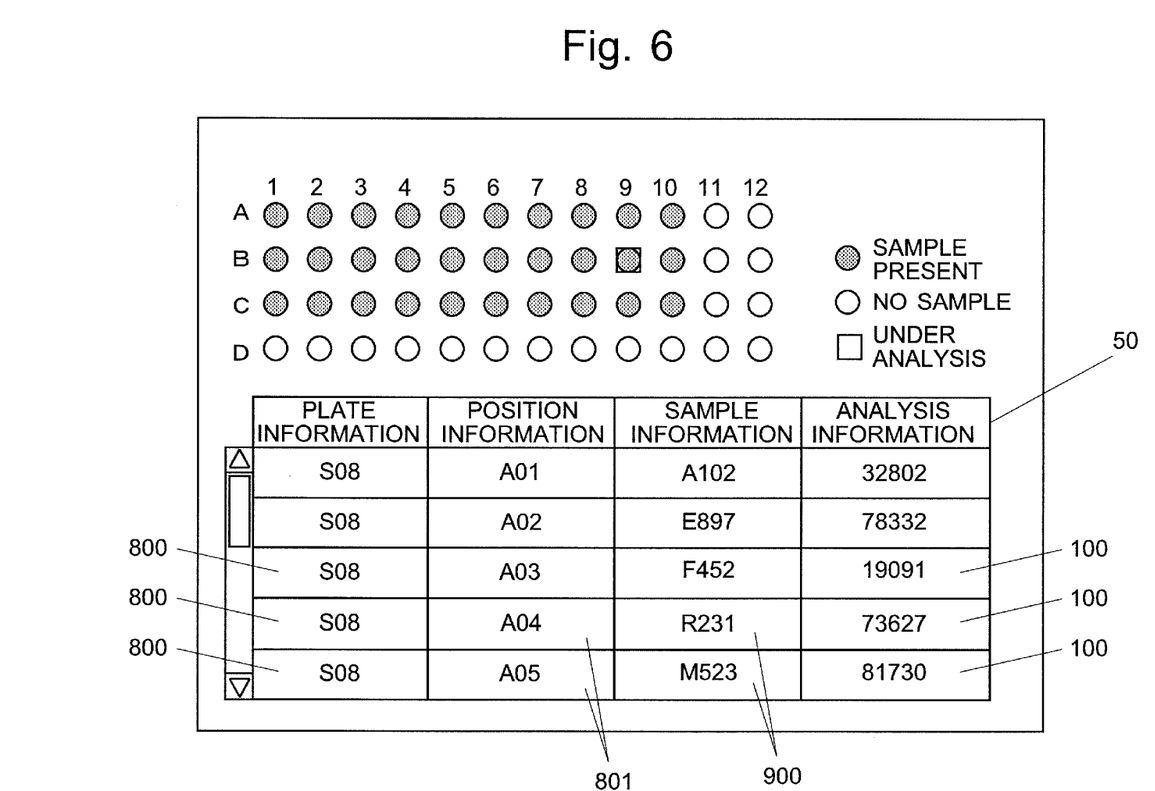
FIG. 6 shows a configuration example of a management screen of a table.

The management screen of the table 50 may display other kinds of information in addition to the contents of the table 50, such as the arrangement of the samples 9 on the sample plate 8 and the progress of the analysis processing, as shown in FIG. 6.

6. Processing Flow

Figure 7:
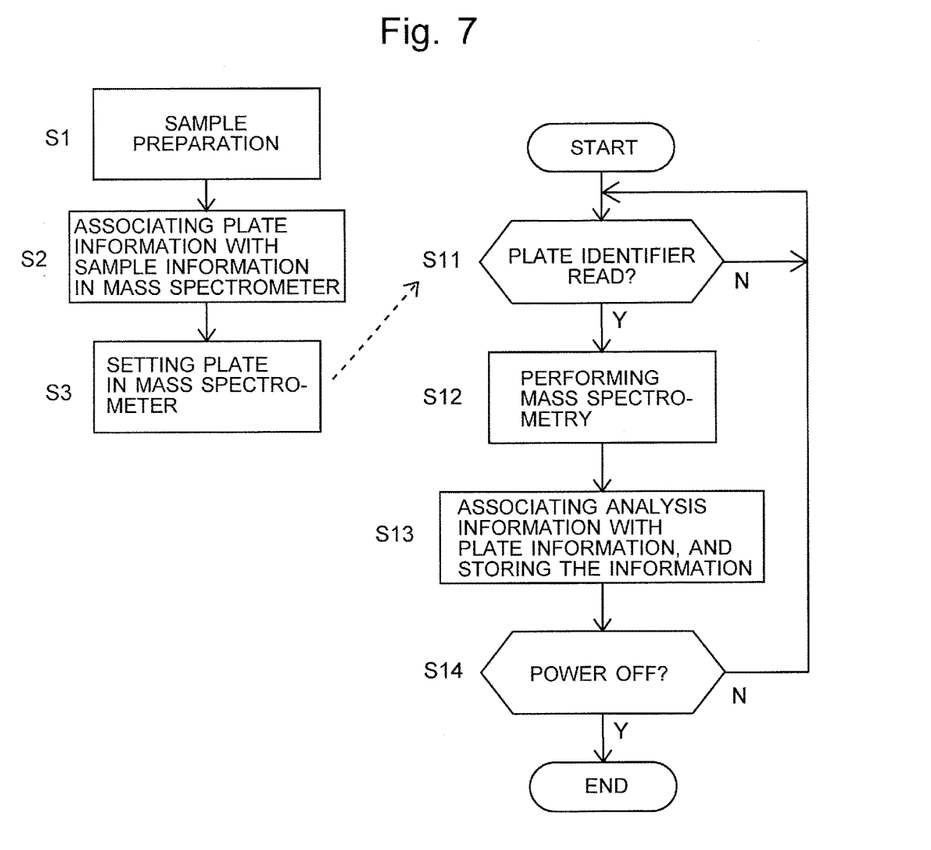
FIG. 7 is a flowchart of the process of performing a mass spectrometric analysis on a sample by the mass spectrometer.

A processing flow of the mass spectrometric analysis performed on the sample 9 by the mass spectrometer 10 is described, with reference to FIG. 7. FIG. 7 includes two flow charts: one shows a work flow for an operator to carry out the mass spectrometric analysis on the sample 9 by the mass spectrometer 10 (Step S1 to Step S3); the other shows a flow of processing carried out in the mass spectrometer 10 (Step S11 to Step S14).

Step S1: First, the sample 9 is placed on the sample plate 8 (sample preparation operation). Specifically, for example, this operation is conducted in such a manner that an operator drops the sample 9 on each of the plurality of concave portions 81 on the sample plate 8.

Step S2: Subsequently, an operation for associating the sample plate 8 (specifically, each of the concave portions 81 of the sample plate 8) with the samples 9 placed thereon in the mass spectrometer 10 is performed. Specifically, this operation is conducted as follows, for example: The operator reads the plate identifier 80 provided on the sample plate 8 with a handheld reading device (a handheld barcode reader, for example) and sends the read information to the mass spectrometer 10 (in a specific way, the data server 12, for example). In addition, the operator sends, to the mass spectrometer 10, information (position information) 801 for identifying a single concave portion 81 on the sample plate 8. The operator further reads the identifier (identifier indicating the sample information 900) provided in a container or the like of the sample 9 (sample 9 placed on this single concave portion 81) with a handheld reading device (a handheld barcode reader, for example) and sends the read information to the mass spectrometer 10.

The controller 5 of the mass spectrometer 10 interprets the received plate identifier 80 to identify the plate information 800 indicated thereby, and refers to the position information 801 to identify a single concave portion 81. Meanwhile, the controller 5 interprets the received identifier of the sample to identify the sample information 900 indicated thereby. Then, each of the information 800, 801, and 900 is written in a single record in the table 50. Thus, the plate information 800 that is the identification information of the sample plate 8, and the sample information 900 that is the identification information of the sample 9 placed on one of the concave portions 81 (the concave portion indicated by the position information 801) on the sample plate 8, are associated with each other and stored.

Step S3: The sample plate 8 on which the sample 9 is placed is transferred to the mass spectrometer 10. In the mass spectrometer 10, an operator sets the sample plate 8 in the mass spectrometer 10. Specifically, as described earlier, the operator holds the sample plate 8 by pinching the upper and lower sides of the handling area 82, and inserts the sample plate 8 through the insertion port 1, so as to place the sample plate 8 on the stage 3 (the stage 3 disposed at the initial position).

Step S11: In the mass spectrometer 10, while the power is switched on, the reading operation by the reading device 6 is continuously carried out (in other words, the light emitter 61 is in the ON state), and the controller 5 monitors the presence and absence of the sample plate 8, based on the information obtained by the reading device 6.

In other words, when the door 2 is in the opened state and the sample plate 8 is not placed on the stage 3 disposed at the initial position, the reading device 6 reads the blank identifier 70, as mentioned above (as shown in FIG. 5). While the reading device 6 reads the blank identifier 70, the controller 5 determines that there is no sample plate 8 inserted through the insertion port 1.

When the sample plate 8 is placed on the stage 3 disposed at the initial position (specifically, when an operator inserts the sample plate 8 through the insertion port 1 to place it on the stage 3, and withdraws his/her hand from the handling area 82), the reading device 6 reads the plate identifier 80 provided on the sample plate 8, as mentioned above (as shown in FIG. 4). When the reading device 6 reads the plate identifier 80, the controller 5 determines that the sample plate 8 inserted through the insertion port 1 is present on the stage 3.

Step S12: When the reading device 6 reads the plate identifier 80 (YES in Step S11), the controller 5 determines that the sample plate 8 inserted through the insertion port 1 is present on the stage 3, and controls the relevant elements of the mass spectrometer 10 to perform the mass spectrometric analysis on the samples 9 on the sample plate 8. Specifically, the analysis is performed as follows under the control of the controller 5: The door 2 is closed, and the pressure in the inner space 110 is reduced. When the inner space 110 reaches a predetermined degree of vacuum, the moving mechanism 4 starts moving the stage 3. Thus, the mass spectrometric analysis is initiated for each of the sample 9 on one of the concave portions 81 on the sample plate 8 that is placed on the stage 3. Upon completion of the mass spectrometric analysis, the stage 3 is returned to the initial position. After the inner space 110 is restored to the atmospheric state, the door 2 is opened.

Step S13: After the mass spectrometric analysis in Step S12 is terminated and the analysis information 100 has been obtained, the controller 5 stores the obtained analysis information 100 in the table 50. More specifically, the controller 5 writes the analysis information 100 in the record in which the plate information 800 indicated by the plate identifier 80 obtained in Step S11 is written. The record into which the obtained analysis information 100 should be written is selected from among a group of records having the same value of the plate information 800 by referring to the position information 801 of the concave portions 81 contained in the analysis information 100 (that is the information for determining which one of the concave portions 81 contains the sample 9 from which the analysis information 100 has been obtained).

With this, the identification information (plate information) 800 of the sample plate 8 and the analysis information 100 of the sample 9 placed on one of the concave portions (the concave portion indicated by the position information 801) 81 of the sample plate 8 are associated with each other and stored. As mentioned above, the plate information 800 and the position information 801 are previously associated with the sample information 900 in the table 50. Accordingly, as a result of the present processing, the sample information 900 and the analysis information 100 are associated with each other and stored in the table 50.

Step S14: Subsequently, the controller 5 determines whether or not the device has been powered OFF. If the device has not been powered OFF (NO in Step S14), the processing returns to Step S11.

7. Effect

In the mass spectrometer 10 according to the above embodiment, when the sample plate 8 is inserted through the insertion port 1, the plate identifier 80 provided in the sample plate 8 is read by the reading device 6. The identification information 800 of the sample plate 8, which is indicated by the read plate identifier 80, is associated with the analysis information 100 of the sample 9 placed on the sample plate 8, to be stored. This configuration eliminates the necessity for an operator of the mass spectrometer 10 to manually read the plate identifier 80 provided in the sample plate 8, thereby preventing human errors, such as the omission of reading and failure of reading. Therefore, the reliability of association between the sample 9 and the corresponding analysis information 100 can be enhanced.

In the case where an operator manually reads the identifier 80 provided on the sample plate 8, a space for placing the reading device, such as a barcode reader, should be secured near the mass spectrometer. In contrast, the mass spectrometer 10 according to the present embodiment eliminates such a necessity.

In the mass spectrometer 10 according to the present embodiment, when the sample plate 8 is not present between the reading device 6 and the blank identifier 70 (i.e., the sample plate 8 inserted through the insertion port 1 is not present on the stage 3), the reading device 6 reads the blank identifier 70. With this, the presence/absence of the sample plate 8 can be detected by using the reading device 6 for reading the identification information of the sample plate 8, without specifically providing a detector or the like for detecting the presence/absence of the sample plate 8.

For the mass spectrometer 10 according to the present embodiment, the plate identifier 80 is a barcode, and the reading device 6 is a barcode reader. Barcodes and barcode readers are small in size and low in cost, thereby contributing to the reduction in size of the mass spectrometer 10 and reduction in manufacturing cost.

8. Another Embodiment

The identifiers (the plate identifier 80 and the blank identifier 70) according to the above-mentioned embodiment are not limited to the barcode, but may be a QR Code® or a string of symbols, such as numbers and letters.

The reading device 6 according to the above-mentioned embodiment casts light onto a target object and receives reflected light from the target object. The reading device may also be a type which casts light onto a target object and receives transmitted light through the target object, so as to optically read the target object. In such a case, the light receiver is disposed on a position opposite from the light emitter across the sample plate 8 inserted through the insertion port 1 (i.e., the sample plate 8 placed on the stage 3 at the initial position). With this configuration, when the sample plate 8 inserted through the insertion port 1 is present on the stage 3 (i.e., the sample plate 8 is placed on the stage 3 at the initial position), the light for reading emitted from the light emitter falls onto the handling area 82 of the sample plate 8, and the light receiver receives the transmitted light having passed through the plate identifier 80 provided in the handling area 82. In the case where this type of reading device is adopted, the plate identifier 80 may be provided in the form of a through hole having a specific shape for identification formed in the handling area 82.

REFERENCE SIGNS LIST

1 . . . Insertion Port
2 . . . Door
3 . . . Stage
4 . . . Moving Mechanism
5 . . . Controller
6 . . . Reading Device
8 . . . Sample Plate
9 . . . Sample
10 . . . Mass Spectrometer
11 . . . Extraction Electrode
12 . . . Data Server
13 . . . Main Unit
31 . . . Notch Area
50 . . . Table
51 . . . Storage Section
60 . . . Light for Reading
70 . . . Blank Identifier
80 . . . Plate Identifier
81 . . . Concave Portion
82 . . . Handling Area
100 . . . Analysis Information
800 . . . Plate Information
801 . . . Position Information
900 . . . Sample Information

The invention claimed is:

1. A mass spectrometer comprising:
an insertion port through which a sample plate is to be inserted;
a reading device including: a light emitter disposed to emit light in such a manner the light falls onto the sample plate inserted through the insertion port; and a light receiver configured to receive light reflected by or transmitted through the sample plate to read an identifier provided on the sample plate;
an analyzer configured to perform a mass spectrometric analysis on a sample placed on the sample plate, to obtain analysis information of the sample; and
a storage section configured to store identification information of the sample plate and the analysis information of the sample placed on the sample plate while the identification information and the analysis information are associated with each other, the identification information being indicated by the identifier read by the reading device, and the analysis information being obtained by the analyzer,
wherein:
the light receiver is configured to receive light reflected from the sample plate, and
an identifier indicating an absence of the sample plate is disposed at a position opposite from the reading device across the sample plate inserted through the insertion port.

2. The mass spectrometer according to claim 1, wherein:
the identifier is a barcode, and
the reading device is a barcode reader.

* * * * *